US012789050B2

(12) United States Patent
Cessor et al.

(10) Patent No.: US 12,789,050 B2
(45) Date of Patent: Nov. 10, 2026

(54) SWIM GOGGLES

(71) Applicant: NIKE, Inc., Beaverton, OR (US)

(72) Inventors: Susan D. Cessor, Lake Oswego, OR (US); Carrie Abbamonto, Portland, OR (US); Erika Gentry, Portland, OR (US)

(73) Assignee: NIKE, Inc., Beaverton, OR (US)

( * ) Notice: Subject to any disclaimer, the term of this patent is extended or adjusted under 35 U.S.C. 154(b) by 0 days.

(21) Appl. No.: 18/930,256

(22) Filed: Oct. 29, 2024

(65) Prior Publication Data

US 2025/0229139 A1 Jul. 17, 2025

Related U.S. Application Data

(60) Provisional application No. 63/686,294, filed on Aug. 23, 2024, provisional application No. 63/620,509, filed on Jan. 12, 2024.

(51) Int. Cl.
*A63B 3/00* (2006.01)
*A63B 33/00* (2006.01)
*A61F 9/02* (2006.01)

(52) U.S. Cl.
CPC .............. *A63B 33/004* (2020.08); *A61F 9/02* (2013.01); *A61F 9/026* (2013.01); *A63B 33/002* (2013.01)

(58) Field of Classification Search
CPC ....... A63B 33/002; A63B 33/004; A61F 9/02; A61F 9/026
USPC .................... 2/428, 440, 430, 442, 446, 426
See application file for complete search history.

(56) References Cited

U.S. PATENT DOCUMENTS

| | | | | |
|---|---|---|---|---|
| 2,390,599 | A * | 12/1945 | Lewis | A61F 9/06 D16/311 |
| 6,505,353 | B2 * | 1/2003 | Sung | A63B 33/006 2/428 |
| 8,042,199 | B2 | 10/2011 | Chiang | |
| 9,156,532 | B2 * | 10/2015 | Shiue | B63C 11/12 |
| D745,081 | S | 12/2015 | Ooba et al. | |
| 9,604,104 | B2 | 3/2017 | Stephens et al. | |
| 9,642,749 | B2 * | 5/2017 | McNeal | G02C 5/122 |
| 9,770,628 | B2 * | 9/2017 | Shiue | A63B 33/004 |
| 9,833,663 | B2 | 12/2017 | DiChiara et al. | |
| D820,345 | S | 6/2018 | Chiang | |
| D831,100 | S | 10/2018 | Chiang | |
| D831,731 | S | 10/2018 | Chiang | |
| D839,950 | S | 2/2019 | Chiang | |
| 10,206,819 | B2 * | 2/2019 | Chiang | A63B 33/004 |
| 10,493,325 | B2 * | 12/2019 | Chiang | A63B 71/10 |

(Continued)

OTHER PUBLICATIONS

Arena Sport. “Air-Speed Goggle.” Accessed: Sep. 27, 2023.https://web.archive.org/web/20200925001657/https://www.arenasport.com/en_us/003150-air-speed-goggle.html.

(Continued)

*Primary Examiner* — Alissa J Tompkins
*Assistant Examiner* — Dakota Marin
(74) *Attorney, Agent, or Firm* — Bookoff McAndrews PLLC

(57) ABSTRACT

Swim goggles with a first eyepiece and a gasket coupled to the first eyepiece. The gasket has an outer radial surface extending along a periphery of the first eyepiece; and a plurality of recessed areas in the outer radial surface, the plurality of recessed areas extending circumferentially around the gasket. The plurality of recessed areas are substantially wave shaped.

20 Claims, 12 Drawing Sheets

(56) References Cited

U.S. PATENT DOCUMENTS

| | | | | |
|---|---|---|---|---|
| 10,576,333 | B2 * | 3/2020 | Chiang ................ | A63B 33/004 |
| D885,472 | S | 5/2020 | Johnson et al. | |
| D885,473 | S | 5/2020 | Johnson et al. | |
| 10,668,326 | B2 * | 6/2020 | Chiang ................ | A63B 33/004 |
| D924,964 | S | 7/2021 | Chiang | |
| 11,890,511 | B2 * | 2/2024 | Chiang ................ | A63B 33/004 |
| 11,911,664 | B2 * | 2/2024 | Chiang ................ | A63B 33/004 |
| 2004/0148684 | A1 * | 8/2004 | Wiedner ................. | A61F 9/026<br>2/428 |
| 2017/0252609 | A1 * | 9/2017 | Chiang .................... | A61F 9/026 |
| 2018/0339197 | A1 * | 11/2018 | Chiang ................ | A63B 33/004 |
| 2019/0070464 | A1 * | 3/2019 | Chiang ................ | A63B 33/004 |
| 2023/0138929 | A1 | 5/2023 | Chiang et al. | |
| 2023/0293947 | A1 * | 9/2023 | Chiang ................ | A63B 33/004<br>2/428 |

OTHER PUBLICATIONS

Arena. "The One Unisex Adults Swim Goggles Men & Women Watertight Fit Orbit-Proof Seals Anti-Fog Coated Mirror/Non-Mirror Lens," amazon.com. Accessed:Sep. 29, 2023.https://www.amazon.com/Arena-Watertight-Orbit-Proof-Anti-Fog-Non-Mirror/dp/B081ZSDWGB?th=1.

Speedo, "Biofuse 2.0." Accessed: Sep. 27, 2023.https://web.archive.org/web/20230326185811/https://us.speedo.com/biofuse-2.0/14009572.html.

Sumarpo. "S1 Goggle," sumarpro.com. Accessed: Sep. 29, 2023. https://www.sumarpo.com/products/s1-goggle?currency=USD&variant=41372174418081&utm_medium=cpc&utm_source=google&utm_campaign=Google%20Shopping&stkn=7e0a4be5634b&gclid=CjwKCAjw69moBhBgEiwAUFCx2Bn3pBnfrf_ujJvhuALm1cbydE0GsjwLSNG44aXVF0A51p8YtA1hfhoCWWgQAvD_BWE.

* cited by examiner

SWIM GOGGLES

CROSS-REFERENCE TO RELATED APPLICATION

This application claims priority under 35 U.S.C. § 119 (e) to Provisional U.S. Patent Application No. 63/686,294, filed Aug. 23, 2024, and Provisional U.S. Patent Application No. 63/620,509, filed Jan. 12, 2024 the disclosure of which is hereby incorporated by reference in its entirety.

TECHNICAL FIELD

The present disclosure relates generally to goggles, and more particularly, to swim goggles.

BACKGROUND

This section provides background information related to the present disclosure which is not necessarily prior art.

Swim goggles are used to isolate a swimmer's eyes from the surrounding water. Conventional swim goggles typically include a pair of spaced-apart eyepieces that are worn over the eyes, a nose band that extends over the nose and connects the eyepieces to one another, and an elastic strap that extends around the rear of the head. Such goggles typically surround the wearer's orbit (eye socket) to protect the eye and improve underwater vision by providing a corneal/air interface instead of exposing the cornea directly to an aqueous environment.

Two important design considerations that drive the design of swim goggles are minimizing hydrodynamic drag and minimizing water entry within the goggle. Hydrodynamic drag creates resistance to the swimmer's forward movement through the water, thereby reducing the swimmer's velocity through the water. Therefore, in order to maximize their velocity when racing or otherwise moving through the water, swimmers need to reduce water resistance or hydrodynamic drag as much as possible. Reducing hydrodynamic drag is of particular importance in sprinting events, such as the 100-meter freestyle, where time differences between swimmers are frequently measured in fractions of a second. Additionally, during swimming, water may enter a frame of the goggles should the goggles not be sufficiently sealed.

Accordingly, there is a continuing need for new and improved swim goggles, and especially for goggles that minimize hydrodynamic drag and/or minimize water entry within the goggles.

DETAILED DESCRIPTION

Figure 1:
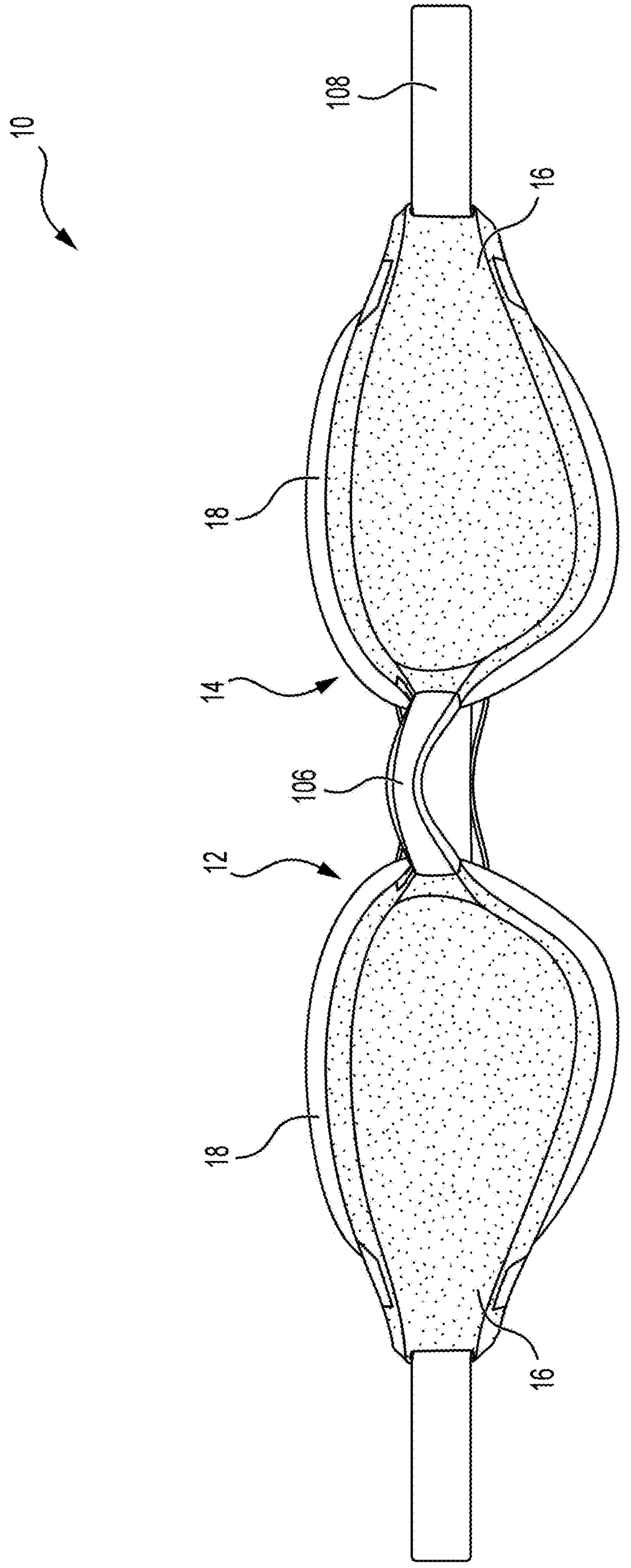
FIG. 1 is a front view of a pair of goggles.
Figure 2:
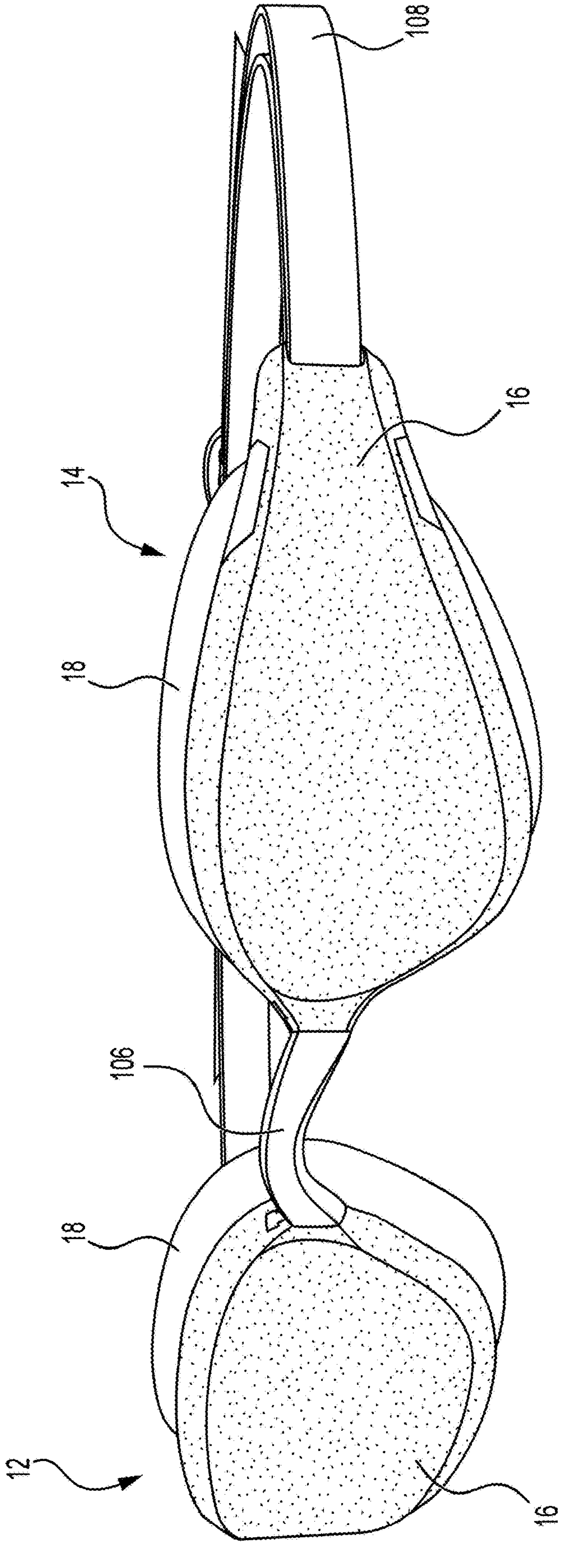
FIG. 2 is a perspective view of the goggles shown in FIG. 1.
Figure 3:
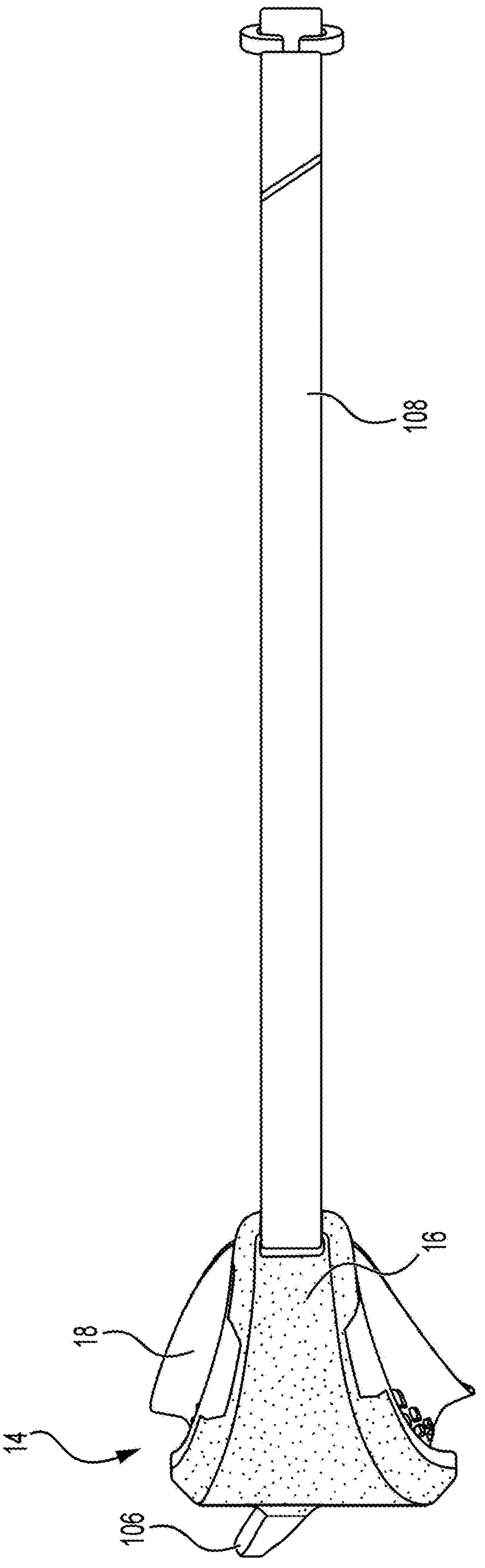
FIG. 3 is a side view of the goggles shown in FIG. 1.
Figure 4:
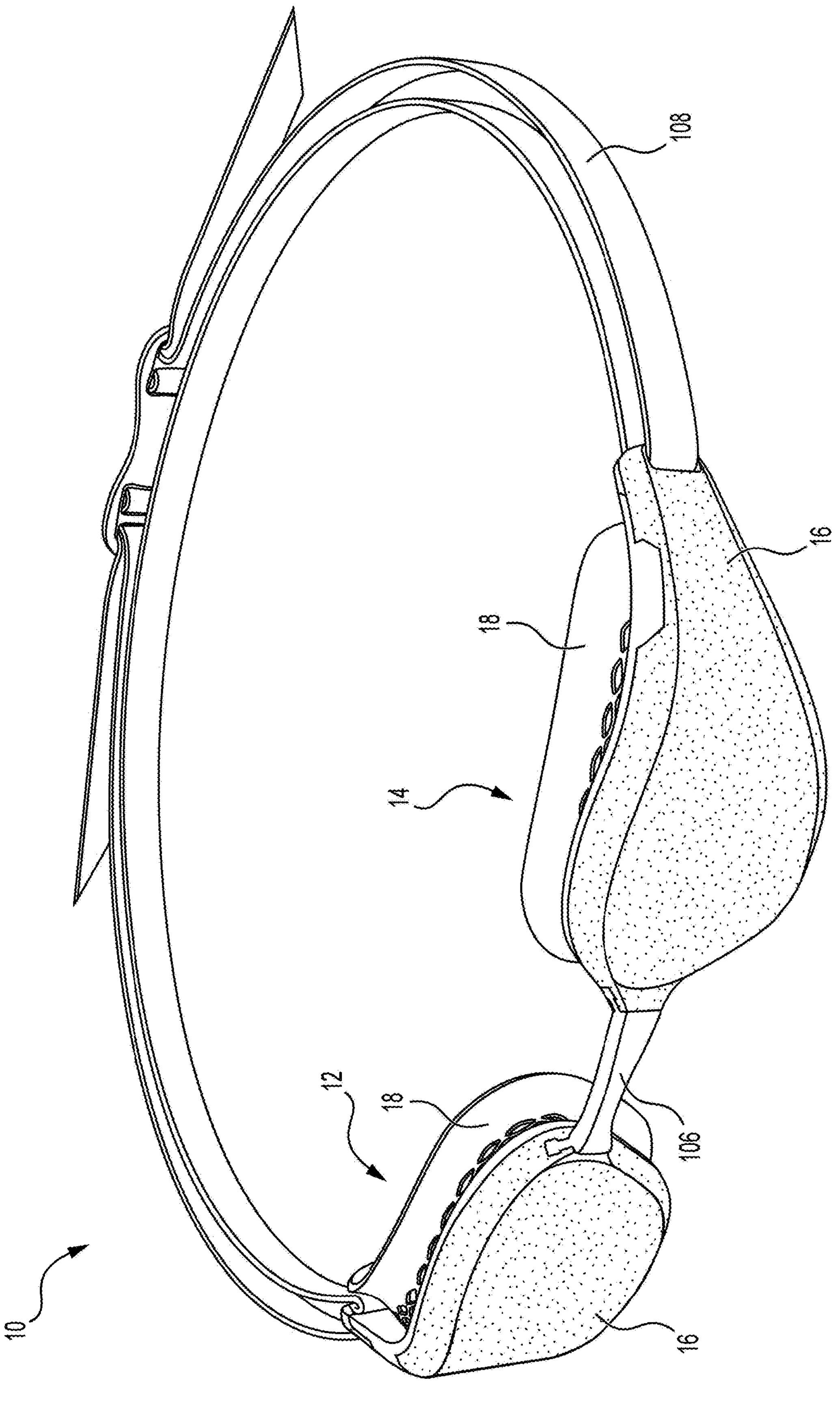
FIG. 4 is a front perspective of the goggles of FIG. 1.

The above features and advantages and other features and advantages of the present teachings are readily apparent from the following detailed description of the modes for carrying out the present teachings when taken in connection with the accompanying drawings.

"A," "an," "the," "at least one," and "one or more" are used interchangeably to indicate that at least one of the items is present. A plurality of such items may be present unless the context clearly indicates otherwise. All numerical values of parameters (e.g., of quantities or conditions) in this specification, unless otherwise indicated expressly or clearly in view of the context, including the appended claims, are to be understood as being modified in all instances by the term "about" whether or not "about" actually appears before the numerical value. "About" indicates that the stated numerical value allows some slight imprecision (with some approach to exactness in the value; approximately or reasonably close to the value; nearly). If the imprecision provided by "about" is not otherwise understood in the art with this ordinary meaning, then "about" as used herein indicates at least variations that may arise from ordinary methods of measuring and using such parameters. In addition, a disclosure of a range is to be understood as specifically disclosing all values and further divided ranges within the range. All references referred to are incorporated herein in their entirety.

The terms "comprising," "including," and "having" are inclusive and therefore specify the presence of stated features, steps, operations, elements, or components, but do not preclude the presence or addition of one or more other features, steps, operations, elements, or components. Orders of steps, processes, and operations may be altered when possible, and additional or alternative steps may be employed. As used in this specification, the term "or" includes any one and all combinations of the associated listed items. The term "any of" is understood to include any possible combination of referenced items, including "any one of" the referenced items. The term "any of" is understood to include any possible combination of referenced claims of the appended claims, including "any one of" the referenced claims.

Those having ordinary skill in the art will recognize that terms such as "above," "below," "upward," "downward," "top," "bottom," etc., are used descriptively relative to the figures, and do not represent limitations on the scope of the invention, as defined by the claims.

In the discussion that follows, terms "about," "approximately," "substantially," and the like, when used in describing a numerical value, denote a variation of +/−10% of that value, unless specified otherwise.

Additionally, the goggles are discussed with the standard of orientation being when worn by a user of the goggles.

FIGS. 1-4 illustrate a set of goggles 10, according to an example, which includes a first (right) eyepiece 12 and a second (left) eyepiece 14, configured to isolate a user's eyes from the surrounding environment. Each eyepiece 12 and 14 comprises a body having a transparent lens portion 16 for covering an eye and a curved peripheral frame portion or gasket 18 surrounding and supporting the lens portion 16. The curve of the gasket 18 substantially conforms to the contour of a human face from the nose to the orbital rims. The gaskets 18 have respective posterior surfaces or cupped portions 26 that are configured to be placed adjacent the skin of the user.

The gaskets 18 may be formed of an overmolded thermoplastic rubber (TPR). In some examples, the gaskets 18 are formed of a silicone or any other suitable molded plastic which is flexible. Each eyepiece 12 and 14 is constructed from a relatively stiff and hard transparent plastic, with good scratch resistance and optical qualities. A suitable plastic includes an impact-resistant polycarbonate material, although various other materials which are scratch resistant and provide good optical quality may be used.

The eyepieces 12 and 14 can have any of various configurations. In an example, a nose piece 106 interconnects adjacent ends of the eyepieces 12 and 14. In the example, a strap 108 is connected to end portions of respective eyepieces 12 and 14. When worn, strap 108 extends around the rear of the head of the user. Other configurations also can be implemented in the goggles. For example, eyepieces 12 and 14 may be formed as unitary and separate components without nose piece 106 and strap 108.

In another example, each lens portion 16 can be formed with a curved, convex anterior surface. In addition, the lens portions 16 can have various tints or coatings (e.g., an anti-reflection coating).

As will be described in greater detail with reference to FIG. 6, the eyepieces 12 and 14, and specifically the gaskets 18, are configured to form a substantially water-tight seal with the face of a wearer in order to keep water away from the wearer's eyes. Additionally, the gaskets 18 of the eyepieces 12 and 14 assist the wearer in retaining the eyepieces 12 and 14 against the face of the wearer. The gaskets 18 are constructed to generally relate to the shape of the orbital rims and orbicularis muscles of the wearer such that at least portions of the gaskets 18 seat against and/or fit just within the orbital rims.

In an embodiment, the gaskets 18 may be sized and shaped in any configuration to fit substantially or entirely within an orbital rim of the wearer. In another embodiment, the gaskets 18 may be sized and shaped in any configuration to reside completely outside the orbital rim of the wearer.

Dimensions of the frame that can be retained by the orbicularis oculi muscles may be determined using many different approaches. For example, the goggles can be custom designed and fitted to a particular individual. Alternatively, the dimensions can be determined by reference to a standard head form that has been designed according to statistical norms from the population, or from published texts and descriptions of such norms.

In an example, each eyepiece 12 and 14 has a one-piece or unitary construction. In an alternative example, the lens portions 16 and the gaskets 18 are separately formed and then subsequently joined together to form the eyepieces 12 and 14. The lens portions 16 can be either permanently attached to the gaskets 18 or connected to the gaskets 18 in a removable manner. In this alternative embodiment, the gaskets 18 need not be constructed from the same material as the lens portions 16.

Figure 5:
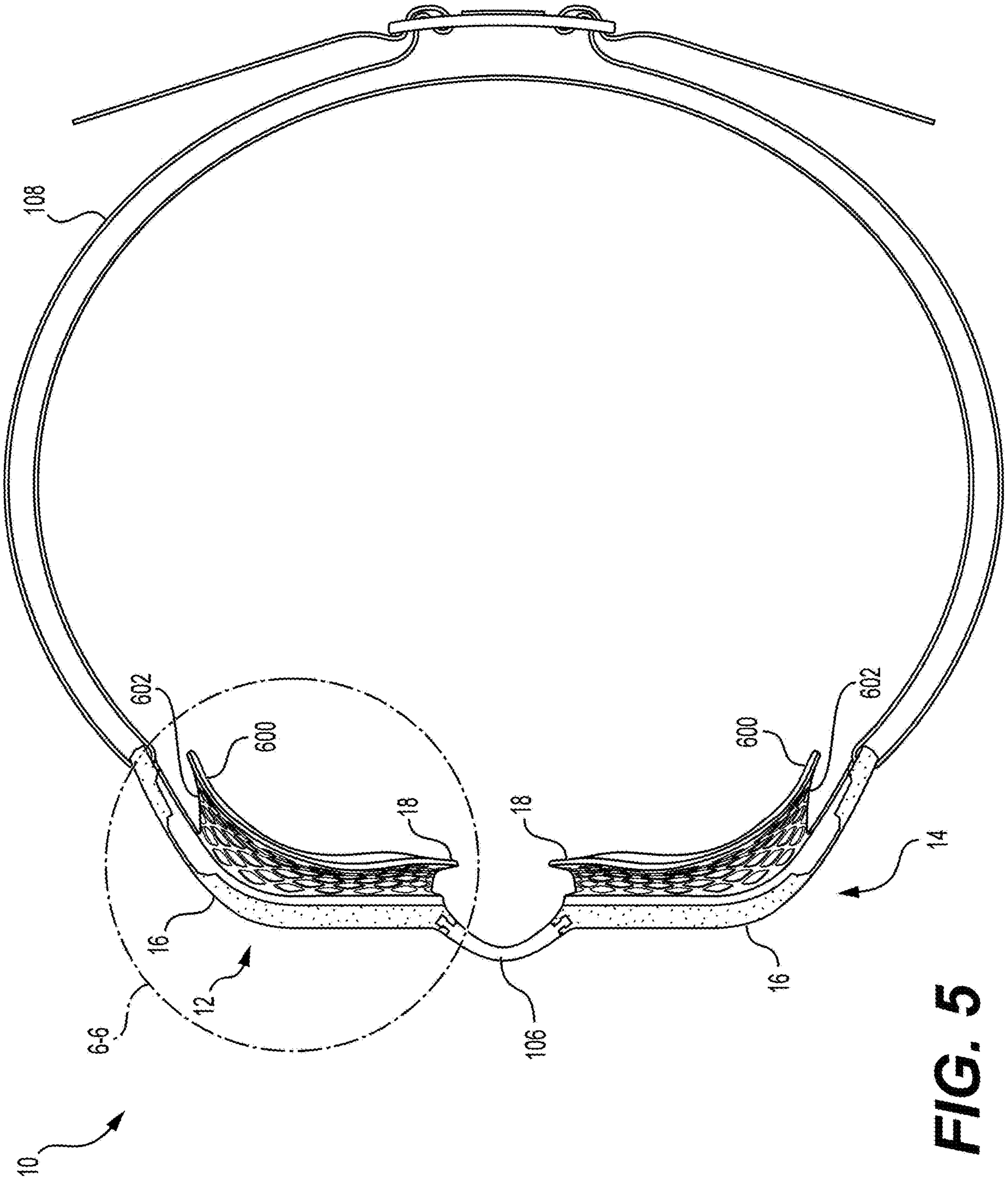
FIG. 5 is a top view of the goggles shown in FIG. 1.
Figure 6:
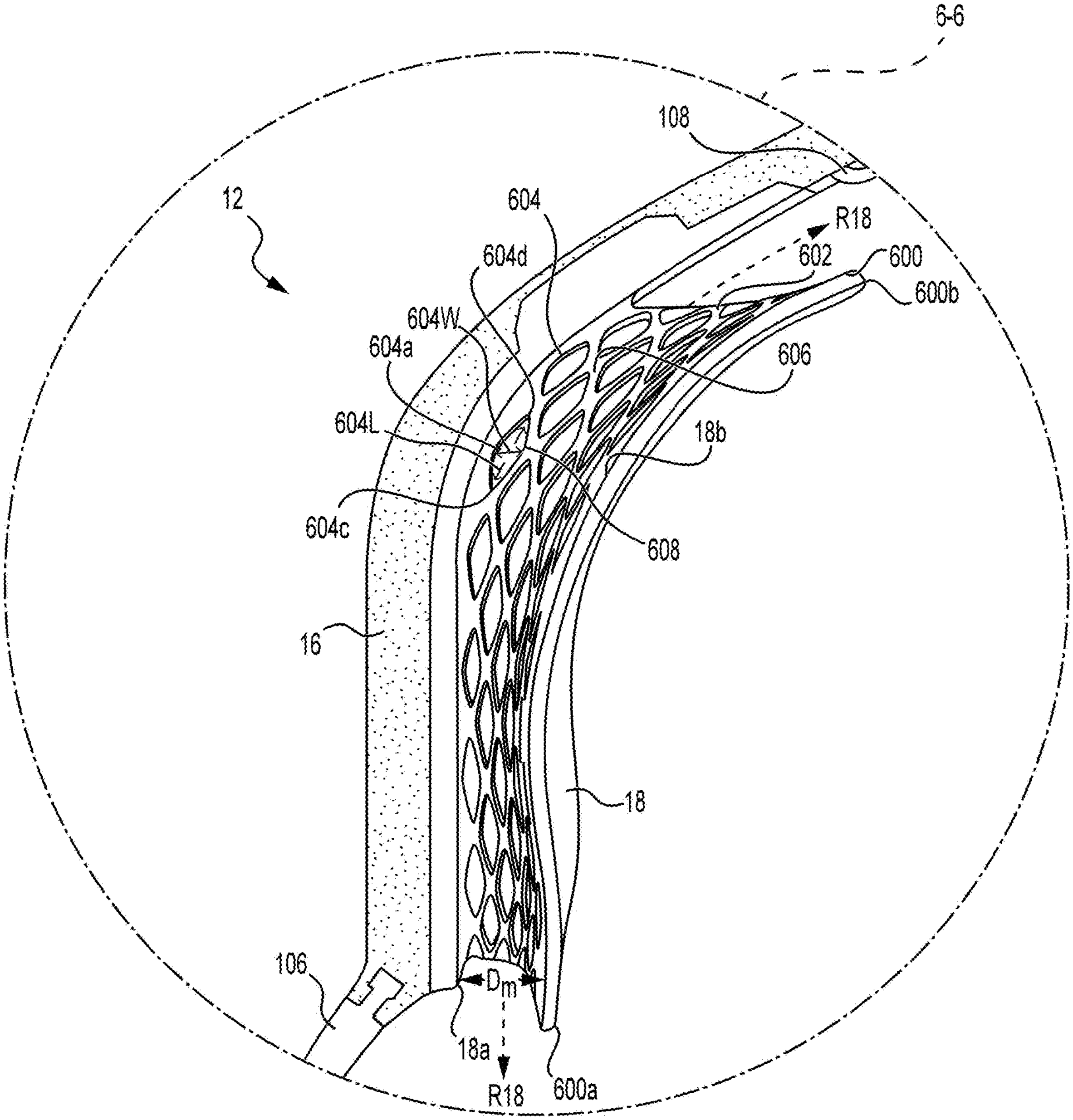
FIG. 6 is an enlargement of the area 6-6 of the goggles of FIG. 5.

Referring to FIGS. 5 and 6, the gasket 18 includes a flange 600, which when worn, abuts a wearer's face. The flange 600 may have a similar curvature as the gasket 18. The flange includes a first end 600*a* and a second end 600*b*. The first end 600*a* is disposed near the nose piece 106. The second end 600*b* is disposed near the strap 108. The gasket 18 includes a first surface 602 and a second surface (not shown) opposite the first surface 602. The gasket 18 also includes a first (posterior) edge 18*a* and a second (anterior) edge 18*b*.

Each gasket 18 has a variable depth in the posterior-anterior direction between the first edge 18*a* and a second edge 18*b*. As shown, each gasket 18 has a depth, Dm, measured between the first edge 18*a* and the second edge 18*b*. The depth Dm decreases between portions of the first edge 18*a* and second edge 18*a* near the first end 600*a*. The depth Dm increases between portions of the first edge 18*a* and second edge 18*b* as the curvature approaches the second end 600*b*. The minimum depth Dm corresponds to a longitudinal length of the first surface 602 of the gasket 18. The minimum depth Dm allows for water to flow more easily and quickly from the forehead over the eyepieces 12 and 14 as the swimmer moves through the water, as well as providing increased and tighter suction to the swimmer's face. In some examples, each gasket 18 has a maximum depth Dm of less than 25 mm. In some examples, each gasket 18 has a maximum depth Dm of about 12 mm. In some examples, each gasket 18 has a maximum depth Dm of about 8 mm. In some examples, each gasket 18 has a maximum depth Dm of about 5.75 mm.

The first (outer radial) surface 602 of the gasket 18 includes a plurality of recesses 604. The plurality of recesses 604 are disposed between the first edge 18*a* and the second edge 18*b*. The plurality of recesses 604 are a portion of the gasket 18 having a thickness less than an adjacent surface of the gasket 18. In an example, the plurality of recesses 604 are recessed relative to the first surface 602 of the gasket 18. In some examples, the entirety of the outer surfaces (recessed and non-recessed portions) are continuous and contain material. In other words, in some embodiments, there are no holes or other gaps extending through the outer radial surfaces of the gasket 18. A respective recess of the plurality of recesses 604 includes an anterior edge 604*a* and a posterior edge 604*b* as well as a first end 604*c* and a second end 604*d*. The anterior edge 604*a* is disposed opposite the posterior edge 604*b*. The plurality of recesses 604 are substantially diamond shaped, with a length greater than a width, as described further below. A width 604W corresponding to a greatest width of a respective one of the plurality of recesses extends perpendicular to the radius of curvature R18. The anterior edge 604*a* and the posterior edge 604*b* form the widest parts of the diamond shape, corresponding to the maximum width 604W. In an example, the anterior edge 604*a* is curved. In an example, the posterior edge 604*b* is curved. In another example, the anterior edge 604*a* is substantially pointed. In another example, the posterior edge 604*b* is substantially pointed. A length 604L of a respective recess of the plurality of recesses 604 extends parallel to a radius of curvature R18. The first end 604*c* and the second end 604*d* form the longest parts of the diamond shape, corresponding to the maximum length 604L.

The pattern of the respective recesses 604 may flow toward an outer edge of the gasket 18 adjacent a temple of the user when worn. As the recesses 604 flow toward the outer edge of the gasket 18, the shape of the recesses 604 increases as it stretches with the geometry of the gasket 18. In other words, a respective length and a respective width of a given recess 604 increases from the inner edge of the gasket 18 adjacent a nose of the user when worn to the outer edge of the gasket 18 adjacent the temple of the user when worn.

In an example, the width 604W is between about 0.05 mm and about 10 mm. In another example, the width 604W is between about 0.075 mm and about 7 mm. In another example, the width 604W is between about 1 mm and 3 mm. In some examples, the width 604W is about 1.5 mm. In some examples, from the first end 600*a* to the second end 600*b*, the width 604W of a respective recess 604 increases. In an example, when the width 604W increases from the first end 600*a* to the second end 600*b*, a recess 604 disposed nearer the first end 600*a* has a width 604W of about 1.23 mm. In an example, when the width 604W increases from the first end 600*a* to the second end 600*b*, a recess 604 disposed nearer the second end 600*b* has a width 604W of about 2 mm. In other examples, the width 604W of a respective recess 604 decreases from the first end 600*a* to the second end 600*b*. In some other examples, the width 604W of the plurality of recesses 604 is consistent from the first end 600*a* to the second end 600*b*.

In an example, the length 604L is between about 0.05 mm and about 15 mm. In another example, the length 604L is between about 0.075 mm and about 10 mm. In another example, the length 604L is between about 1 mm and 7 mm. In some examples, the length 604L is about 4 mm. In some examples, from the first end 600*a* to the second end 600*b*, the length 604L of a respective recess 604 increases. In an example, when the length 604L increases from the first end 600*a* to the second end 600*b*, a recess 604 disposed nearer the first end 600*a* has a length 604L of about 3.66 mm. In an example, when the length 604L increases from the first end 600*a* to the second end 600*b*, a recess 604 disposed nearer the second end 600*b* has a length 604L of about 4.77 mm. In other examples, the length 604L of a respective recess 604 decreases from the first end 600*a* to the second end 600*b*. In some other examples, the length 604L of the plurality of recesses 604 is consistent from the first end 600*a* to the second end 600*b*.

In an example, a first recess disposed adjacent the first end 600*a* includes a length of about 3.66 mm and a width of about 1.23 mm. Following the pattern toward the second end 600*b*, a second recess disposed between the first end 600*a* and the second end 600*b* includes a length of about 4.13 mm and a width of about 1.70 mm. Still following along the pattern toward the second end 600*b*, a third recess disposed adjacent the second end 600*b* includes a length of about 4.77 mm and a width of about 2.00 mm. It is contemplated that the plurality of recesses 604 may include any shape such as square, oval, rectangular, pointed diamond, or the like.

The plurality of recesses 604 are arranged in a plurality of rows along the first surface 602. Specifically, the plurality of rows of recesses 604 divide the first surface 602 into a thicker anterior portion 602*a*, a thinner middle portion 602*b*, and a thicker posterior portion 602*c*. The thinner middle portion 602*b* is formed by the rows of the plurality of recesses 604 and portions of the first surface 602 between respective rows of the plurality of recesses 604. Both the thicker anterior portion 602*a* and the thicker posterior portion 602*c* are formed only by the first surface 602. In an example, the plurality of recesses 604 are arranged in six rows between the first edge 18*a* and the second edge 18*b*. Respective adjacent recesses 604 in a given row are separated by spaces 606. Rows of recesses 604 are separated from adjacent rows by ribs 608. In another example, the plurality of recesses 604 are arranged in 4 rows between the first edge 18*a* and the second edge 18*b*. In another example, the plurality of recesses 604 are arranged in any number of rows to cover a desired surface area of the first surface 602 between the first edge 18*a* and the second edge 18*b*. In an example, the plurality of recesses 604 are portions of the first surface 602 recessed relative to a thickest portion of gasket 18.

Adjacent rows of the plurality of recesses 604 include individual recesses 604 which are circumferentially staggered relative to one another. In some examples, the space between staggered recesses 604 is between about 0.025 mm and about 2 mm. In some examples, the space between staggered recesses 604 is between about 0.075 mm and about 1 mm. In an example, the space between staggered recesses 604 is about 0.59 mm. Additionally, adjacent individual recesses 604 in a given row are laterally spaced apart from one another. In some examples, the space between laterally adjacent recesses 604 is between about 0.05 mm and about 3 mm. In some examples, the space between laterally adjacent recesses 604 is between about 1 mm and about 2 mm. In an example, the space between laterally adjacent recesses 604 is about 1.8 mm.

The gasket 18 includes a first thickness and a second thickness. The first thickness corresponds to portions of the gasket 18 that are free of the recesses 604 (e.g., non-debossed regions). The first thickness may extend between an outermost row of the plurality of rows of the plurality of recesses 604 near the first edge 18*a* and the first edge 18*a*. The first thickness may also extend between an outermost row of the plurality of rows of the plurality of recesses 604 near the second edge 18*b* and the second edge 18*b*. The first thickness ranges from between about 0.05 mm to about 3 mm. In some examples, the first thickness is between about 0.075 mm and about 1.5 mm. In an example, the first thickness is about 1.15 mm. The second thickness corresponds to portions of the gasket 18 including the recesses 604. The second thickness ranges from between about 0.025 mm to about 1.25 mm. In some examples, the second thickness is between about 0.075 mm and about 1 mm. In an example, the second thickness is about 0.8 mm. In some examples, the second thickness may be a percentage of the first thickness. For example, the second thickness may be 75% of the thickness of the first thickness. As another example, the second thickness may be 50% of the thickness of the first thickness. As another example, the second thickness may be 25% of the thickness of the first thickness. The second thickness may be any percentage less than 100% of the thickness of the first thickness.

The location of the plurality of recesses 604 along the gasket 18 provides the goggles 10 with an improved watertight seal, for example, during a swimming motion. Additionally, the symmetrical nature of the plurality of recesses 604 allows the gasket 18 to move naturally with the user. The reduction of thickness via the plurality of recesses 604 improves comfortability and flexibility of the goggles 10.

Figure 7:
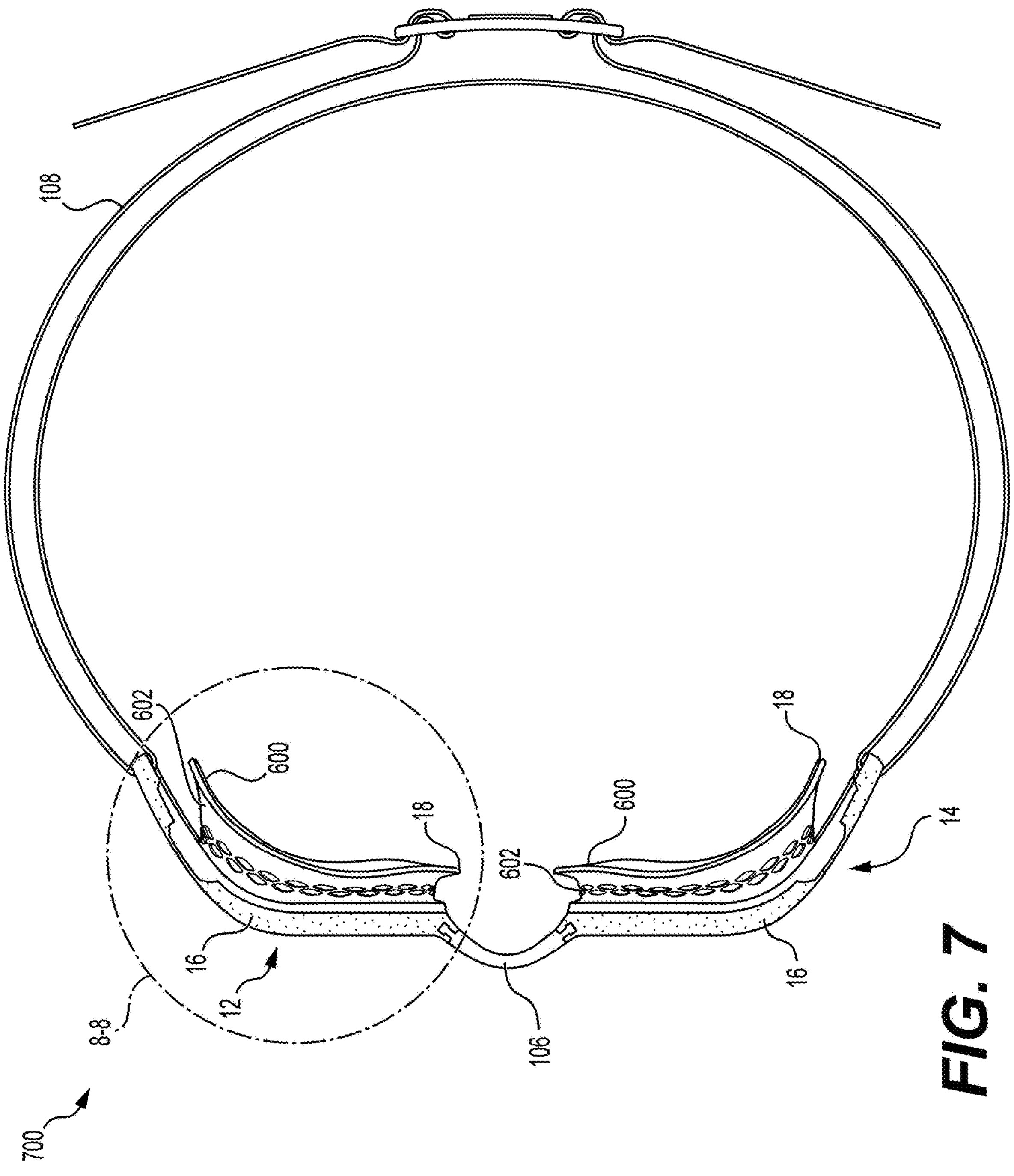
FIG. 7 is a top view of an alternative embodiment of a pair of goggles.
Figure 8:
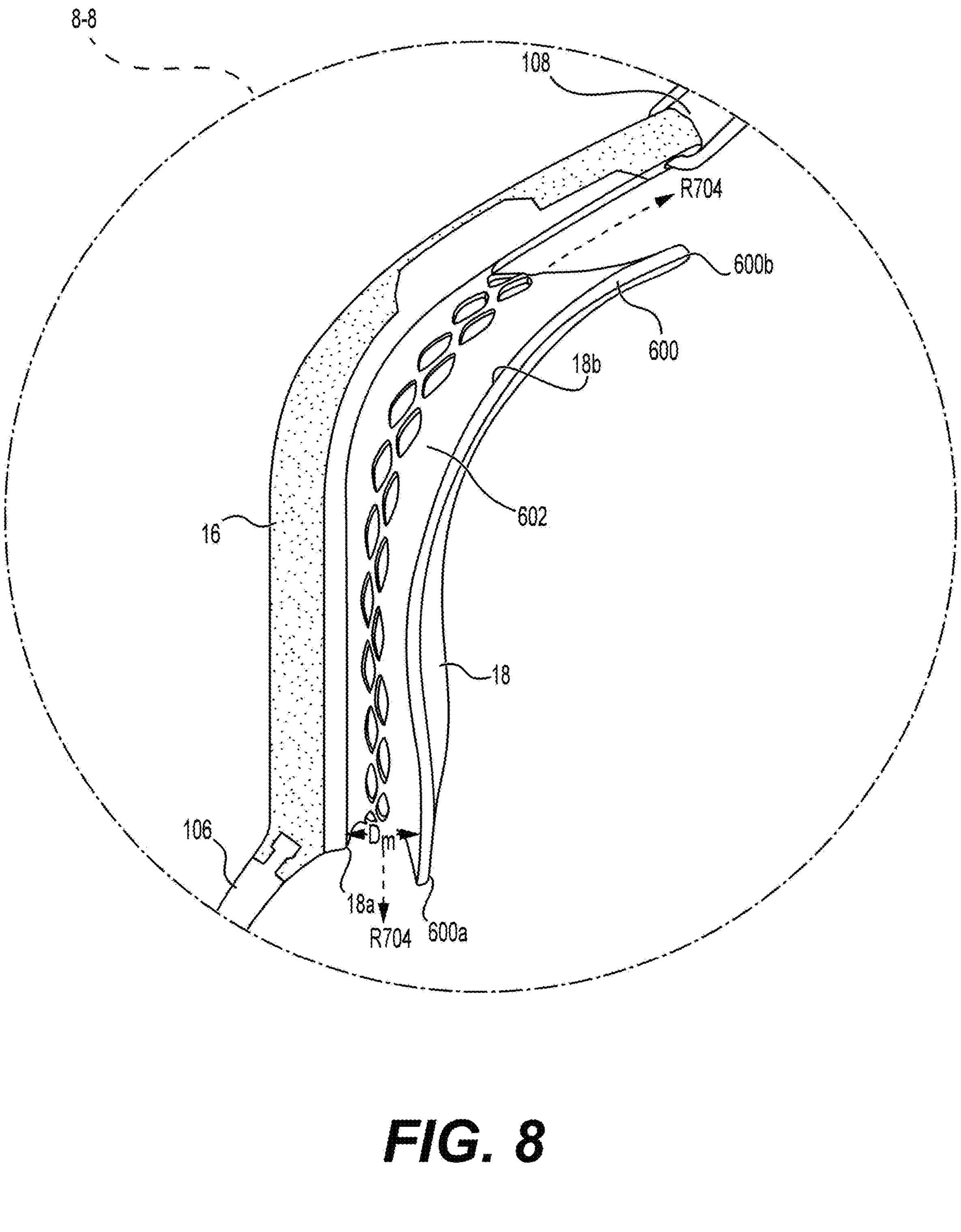
FIG. 8 is an enlargement of the area 8-8 of the goggles of FIG. 7.

Referring to FIGS. 7 and 8, an alternative embodiment of the goggles 10 is shown as goggles 700. Goggles 700 are similar in construction to goggles 10 except as indicated below. Goggles 700 include a plurality of recesses 704. The plurality of recesses 704 are similarly disposed on the first surface 602 as recesses 604, but the plurality of recesses 704 only extend in two rows following a radius of curvature R704 disposed centrally along the gasket 18.

Figure 9:
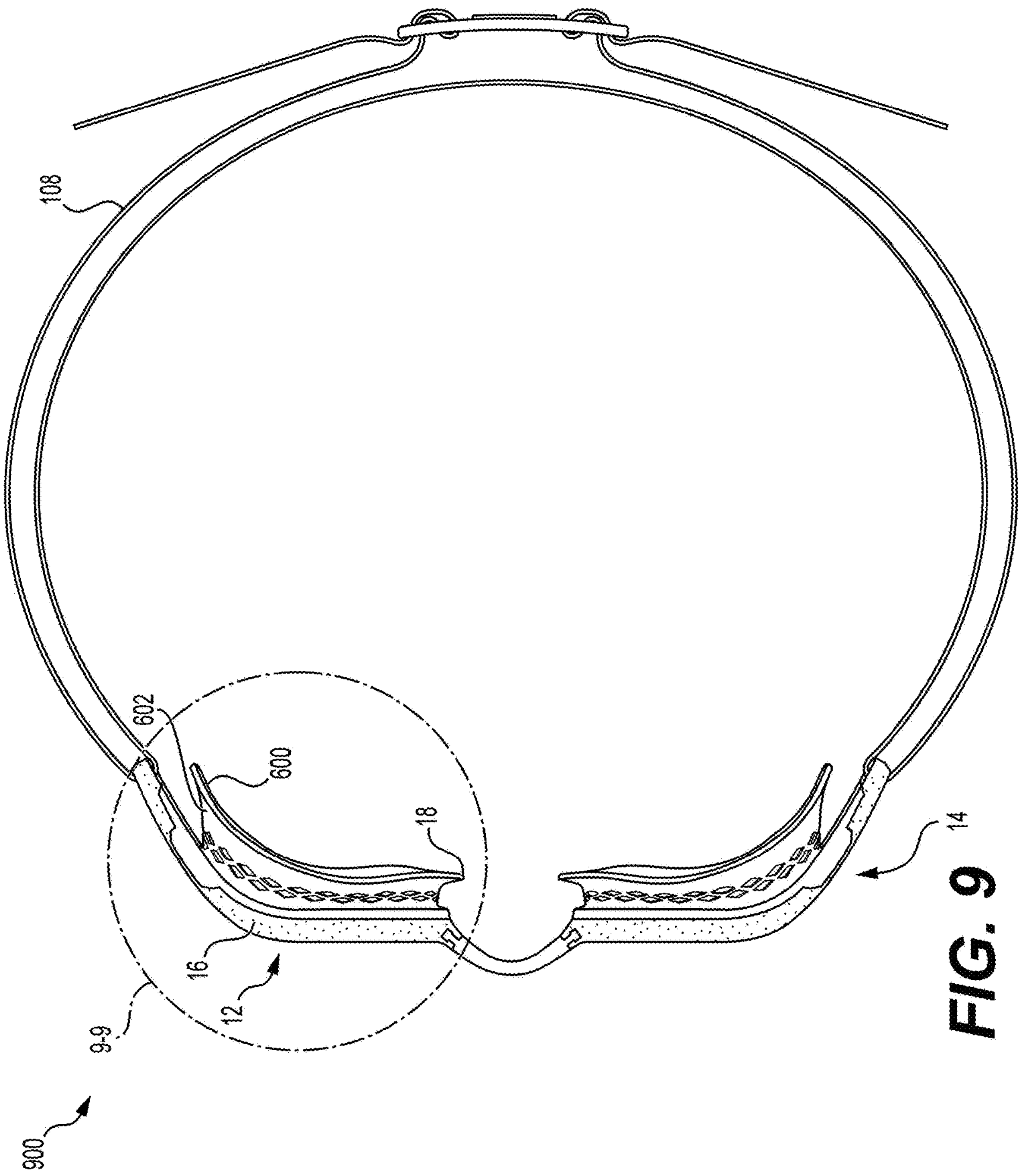
FIG. 9 is a top view of an alternative embodiment of a pair of goggles.
Figure 10:
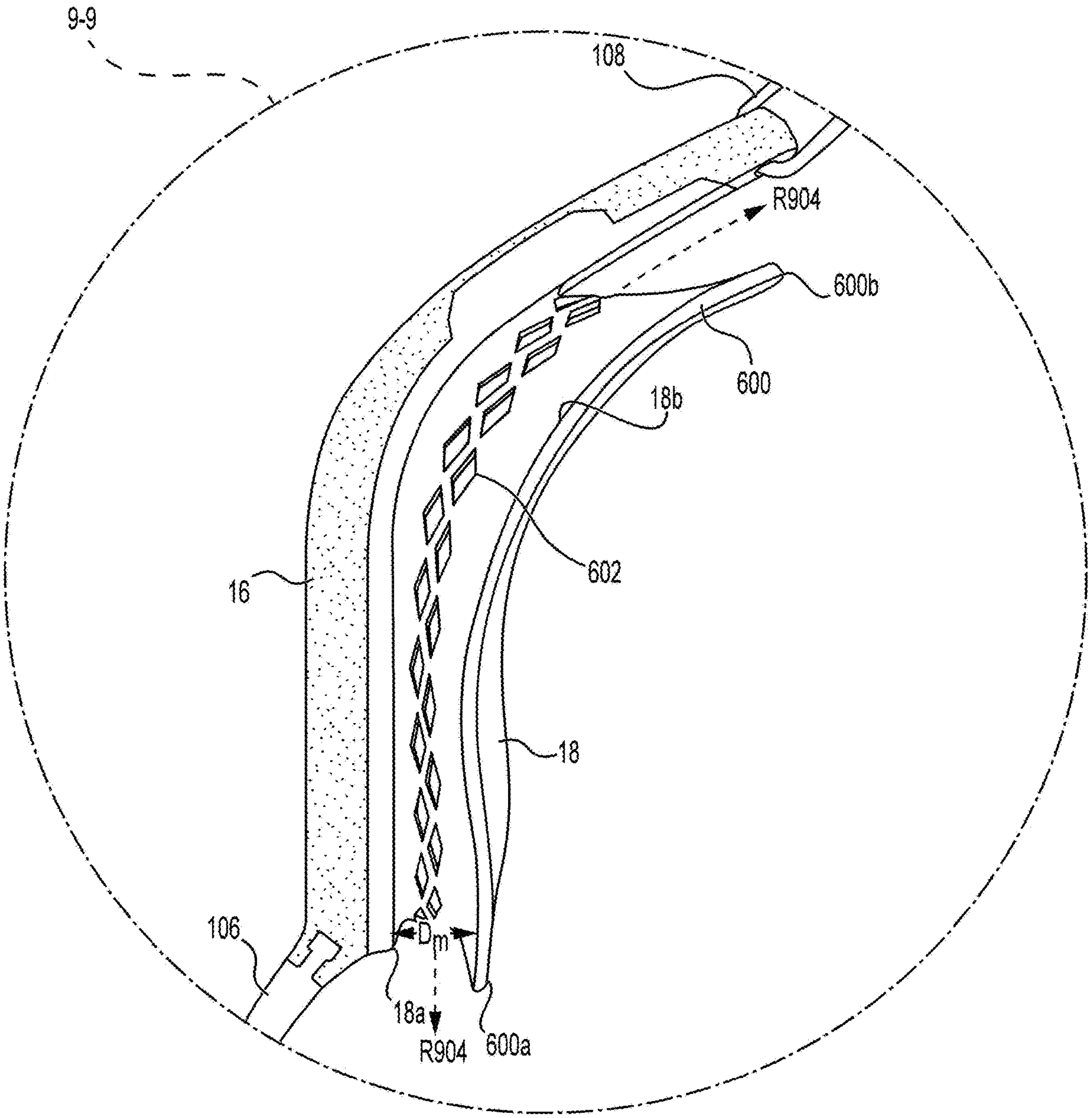
FIG. 10 is an enlargement of the area 9-9 of the goggles of FIG. 7.

FIGS. 9 and 10 show an alternative embodiment of the goggles 10 shown as goggles 900. Goggles 900 are similar in construction to goggles 700 except as indicated below. The goggles 900 include a plurality of recesses 904. The plurality of recesses 904 are similarly disposed on the first surface 602 as recesses 704, but the plurality of recesses 904 include a diamond shape with sharper edges than that of the recesses 704.

Figure 11:
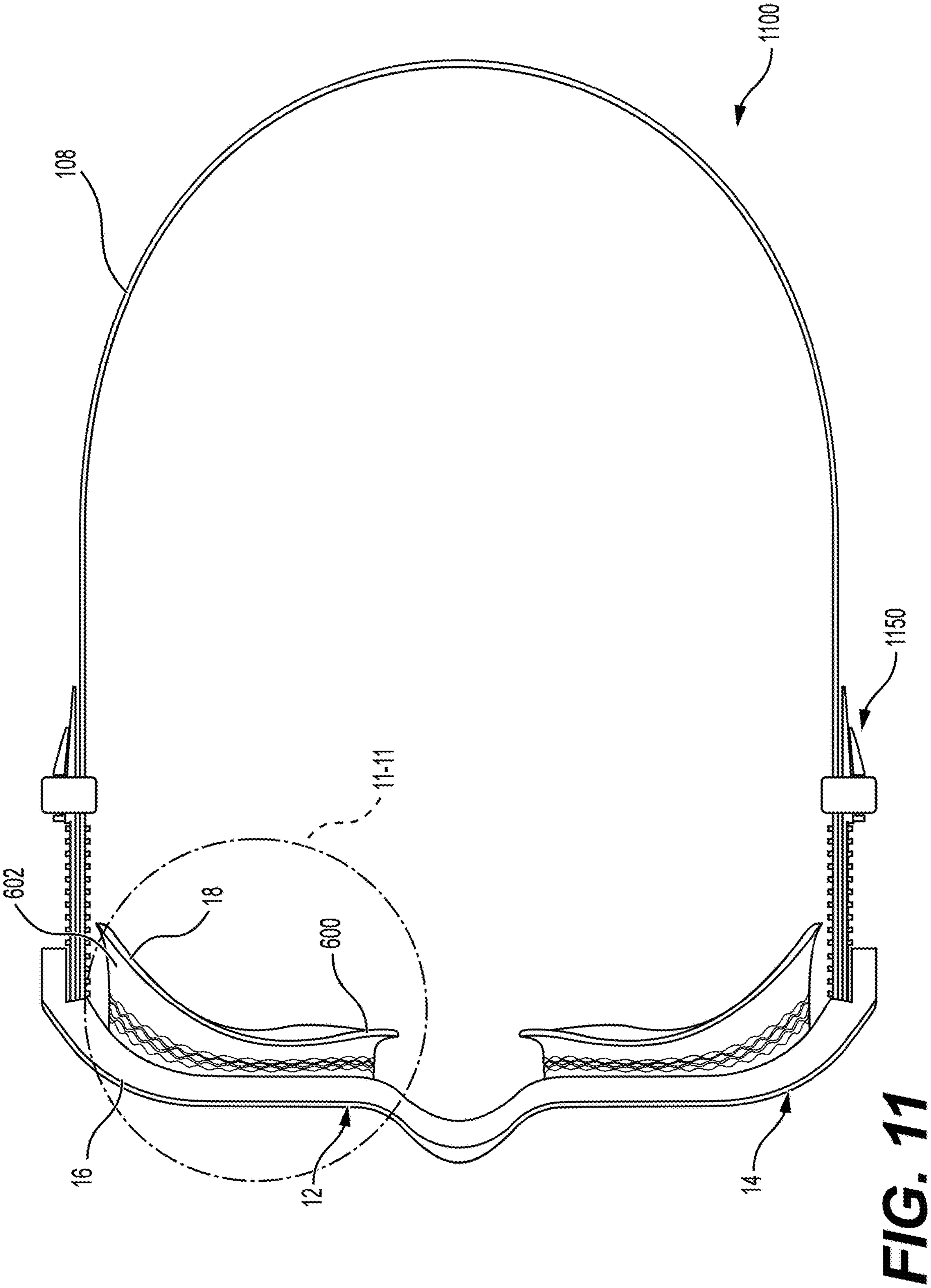
FIG. 11 is a top view of an alternative embodiment of a pair of goggles.
Figure 12:
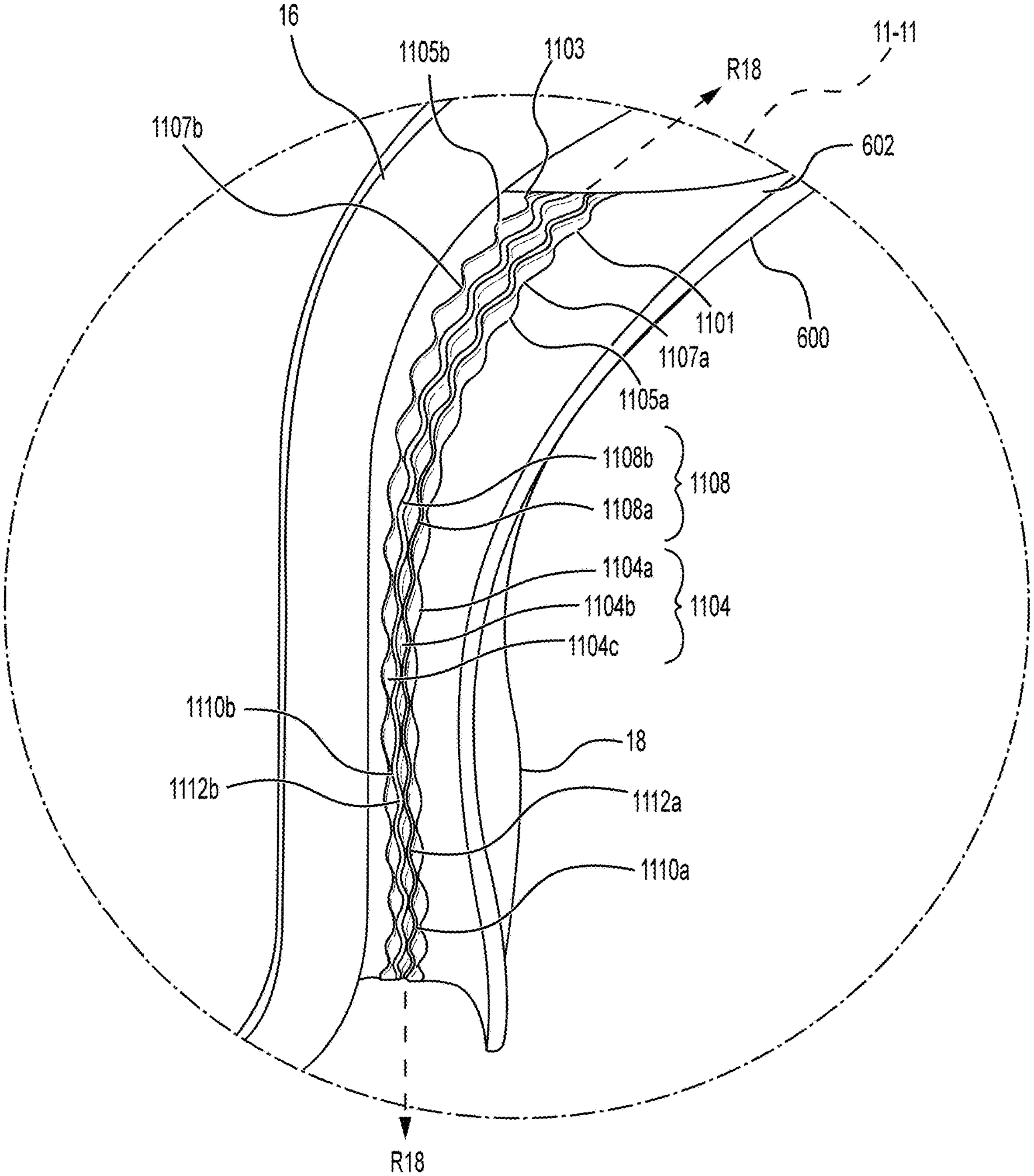
FIG. 12 is an enlargement of the area 11-11 of the goggles of FIG. 7.

FIGS. 11 and 12 show an alternative embodiment of the goggles 10 shown as goggles 1100. Goggles 1100 are similar in construction to goggles 10 except as indicated below. The goggles 1100 include an adjustment mechanism 1150 coupled with the strap 108. The goggles 1100 include a plurality of recessed areas 1104. The plurality of recessed areas 1104 are similarly disposed on the first surface 602 as recesses 604 of the goggles 10.

In some examples, the plurality of recessed areas 1104 are arranged in a plurality of rows along the first surface 602. In an example, the plurality of recessed areas 1104 are recessed portions of the gasket 18 such that the plurality of rows of recessed areas 1104 divide the first surface 602 into thicker outer portions 1106 and one or more bands 1108. The bands 1108 are formed by and between the rows of the plurality of recessed areas 1104 such that the bands 1108 are formed only by the first surface 602. In other words, respective adjacent recessed areas 1104 in a given row are separated by the bands 1108. In an example, the number of rows of the plurality of recessed areas is three. In an example, the plurality of recessed areas 1104 include a first recessed area **1104*a*, a second recessed area 1104*b*, and a third recessed area 1104*c*. The first recessed area 1104*a* includes a posterior edge 1101. The third recessed area 1104*c* includes an anterior edge 1103. The posterior edge 1101 resembles a wave shape. The posterior edge 1101 includes crests 1105*a* and troughs 1107*a*. The anterior edge 1103 resembles a wave shape. The anterior edge 1103 includes crests 1105*b* and troughs 1107*b***.

In an example, the plurality of recessed areas 1104 are divided into between two to six rows. In an example, the plurality of recessed areas 1104 are divided into three rows (as FIGS. 11 and 12 show). In another example, the plurality of recessed areas 1104 are arranged in any number of rows to cover a desired surface area of the first surface 602. Any number of rows of the plurality of recessed areas 1104 may be used as desired to reduce an overall thickness of the gasket 18.

The one or more bands 1108 generally resemble the shape of a wave. For example, the one or more bands 1108 undulate between respective edges 1105 and 1107 of the plurality of recessed areas 1104. The one or more bands 1108 form crests 1110 and troughs 1112 circumferentially disposed along the gasket 18. In an example, the bands 1108 are divided by the recessed areas 1104 into a first band **1108*a* and a second band 1108*b*. The first band 1108*a* is disposed between the first recessed area 1104*a* and the second recessed area 1104*b*. The second band 1108*b* is disposed between the second recessed area 1104*b* and the third recessed area 1104*c*. The first band 1108*a* is disposed nearer the posterior edge 1101 than is the second band 1108*b***.

Each respective band **1108*a* and 1108*b* includes respective crests 1110 and troughs 1112. The first band 1108*a* includes crests 1110*a* and troughs 1112*a*. The second band includes crests 1110*b* and troughs 1112*b*. In an example, when extending tangentially with the radius of curvature R18, crests 1110*a* of the first band 1108*a* are disposed adjacent respective troughs 1107*a* of the posterior edge 1101. The troughs 1112*a* of the first band 1108*a* are disposed adjacent respective crests 1110*b* of the second band 1108*b*. The crests 1110*b* of the second band 1108*b* are disposed adjacent respective troughs 1112*a* of the first band 1108*a*. The troughs 1112*b* of the second band 1108*b* are disposed adjacent respective crests 1105*b* of the anterior edge 1103. In can be said that in some examples, the first band 1108*a* and the second band 1108*b* resemble a destructive interference wave pattern between the anterior edge 1103 and the posterior edge 1101. It is contemplated that in alternative embodiments, the first band 1108*a* and the second band 1108*b* could resemble a constructive interference wave pattern between the anterior edge 1103 and the posterior edge 1101**.

The pattern of the respective recessed areas 1104 and bands 1108 may flow toward an outer edge of the gasket 18 adjacent a temple of the user when worn. As the recessed areas 1104 and the bands 1108 flow toward the outer edge of the gasket 18, the distance between opposing troughs and crests of the posterior edge 1101, the anterior edge 1103, the recessed areas 1104, and the bands 1108 increases as it stretches with the geometry of the gasket 18. In other words, a respective amplitude and a respective wavelength of a given recessed area 1104 and respective band 1108 increases from the inner edge of the gasket 18 adjacent a nose of the user when worn, to the outer edge of the gasket 18 adjacent the temple of the user when worn.

The goggles 10 include a unique debossed design pattern for the gasket 18. The gasket 18 has been engineered with a targeted area of thinner material that flows across the center of the gasket 18 in a substantially diamond pattern. The placement of the targeted area of thinner material preserves and reinforces the watertight seal of the goggles 10 while the body is in motion (while the craniofacial muscles are completing the breathing cycle). The targeted area of thinner material that flows across the center of the gasket 18 facilitates greater compression of thicker portions of the gasket 18, providing the wearer with a cushioned comfortable watertight fit.

The debossed pattern at the center of the gasket 18 creates a thinner band that promotes added flexibility and compression of the entire gasket 18. The added flexibility allows the gasket material to move in tandem with the craniofacial muscles as the swimmer completes the breathing cycle, without breaking the watertight seal. The added compression resulting from the thinner gasket center, creates a natural 'squeeze' effect that gently cradles and cups the eye socket. The symmetrical diamond pattern application ensures the gasket center thickness is reduced proportional to the eye circumference.

The detailed description and the drawings or figures are supportive and descriptive of the present teachings, but the scope of the present teachings is defined solely by the claims. While some of the best modes and other embodiments for carrying out the present teachings have been described in detail, various alternative designs and embodiments exist for practicing the present teachings defined in the appended claims.

While various embodiments have been described, the description is intended to be exemplary, rather than limiting and it will be apparent to those of ordinary skill in the art that many more embodiments and implementations are possible that are within the scope of the embodiments. Any feature of any embodiment may be used in combination with or substituted for any other feature or element in any other embodiment unless specifically restricted. Accordingly, the embodiments are not to be restricted except in light of the attached claims and their equivalents. Also, various modifications and changes may be made within the scope of the attached claims. Benefits, other advantages, and solutions to problems, and any element or elements that may cause any benefit, advantage, or solution to occur or become more pronounced, however, are not to be construed as critical, required, or essential features or elements of any or all of the claims, unless such benefits, advantages, solutions, or elements are expressly stated in such claims.

The following clauses provide an exemplary configuration for an article of footwear and sole structure described above.

Clause 1. Swim goggles comprising: a first eyepiece; and a gasket coupled to the first eyepiece, the gasket including: an outer radial surface extending along a periphery of the first eyepiece; and a plurality of recessed areas in the outer radial surface, the plurality of recessed areas extending circumferentially around the gasket; wherein the plurality of recessed areas are substantially wave shaped.

Clause 2. The goggles of Clause 1, wherein each recessed area divides the outer radial surface into outer portions and one or more bands.

Clause 3. The goggles of Clause 2, wherein the plurality of recessed areas include a first recessed area, a second recessed area, and a third recessed area, and wherein the one or more bands includes a first band and a second band.

Clause 4. The goggles of Clause 3, wherein the first band is disposed between the first recessed area and the second recessed area, and the second band is disposed between the second recessed area and the third recessed area.

Clause 5. The goggles of Clause 1, wherein the plurality of recessed areas are arranged in adjacent circumferential rows.

Clause 6. The goggles of Clause 1, wherein the plurality of recessed areas extend along 30-90% of a posterior-anterior length of the gasket.

Clause 7. The goggles of Clause 1, wherein the gasket includes a thermoplastic rubber.

Clause 8. The goggles of Clause 1, wherein the plurality of recessed areas are divided into circumferential rows, and a number of circumferential rows including two to six rows.

Clause 9. A gasket for swim goggles, the gasket comprising: an outer radial surface extending along a periphery of the gasket; a plurality of recessed areas in the outer radial surface, the plurality of recesses extending circumferentially around the gasket and extending from an anterior edge and a posterior edge; and one or more bands disposed between the plurality of recessed areas, wherein the plurality of recessed areas and the one or more bands are substantially wave shaped.

Clause 10. The gasket of Clause 9, wherein each of the plurality of recessed areas includes at least one crest and at least one trough, and wherein each of the one or more bands includes at least one crest and at least one trough.

Clause 11. The gasket of Clause 10, wherein a first crest of the at least one crests of the one or more bands is disposed between a first trough and a second trough of the at least one troughs of the plurality of recessed areas.

Clause 12. The gasket of Clause 10, wherein the one or more bands includes a first band and a second band, wherein a trough of the first band is disposed adjacent a crest of the second band.

Clause 13. The gasket of Clause 9, wherein the wave shape of the one or more bands and the wave shape of the plurality of recessed areas resembles a destructive wave pattern.

Clause 14. The gasket of Clause 9, wherein a distance between portions of the respective one or more bands and plurality of recessed areas increase at an outer edge of the gasket.

Clause 15. The gasket of Clause 9, wherein the plurality of recessed areas and one or more bands extend along 30-90% of a posterior-anterior length of the gasket.

Clause 16. The gasket of Clause 9, wherein the gasket includes a thermoplastic rubber.

Clause 17. The gasket of Clause 9, wherein the one or more bands and plurality of recessed areas are divided into a plurality of circumferential rows around the outer radial surface, and wherein the plurality of circumferential rows includes two to six rows.

Clause 18. The gasket of Clause 9, wherein the gasket includes a silicone.

Clause 19. Swim goggles including the gasket of Clause 9.

We claim:

1. Swim goggles comprising:

a first eyepiece; and a gasket coupled to the first eyepiece, the gasket including:

an exterior radial surface extending along an outer periphery of the first eyepiece;

an interior radial surface disposed opposite the exterior radial surface, the interior radial surface extending along an inner periphery of the first eyepiece; and a plurality of recessed areas disposed within the exterior radial surface of the gasket, the plurality of recessed areas extending circumferentially along the gasket;

wherein the plurality of recessed areas are substantially wave shaped, wherein the recessed areas of the plurality of recessed areas divide the outer radial surface into two or more bands, each of the bands including at least one crest and one trough, and the bands are separate bands spaced apart from one another by the recessed areas.

2. The goggles of claim 1, wherein the exterior radial surface includes outer portions and the plurality of recessed areas disposed between the outer portions.

3. The goggles of claim 1, wherein the plurality of recessed areas include a first recessed area, a second recessed area, and a third recessed area, and wherein the plurality of recessed areas are divided into two or more bands including at least a first band and a second band.

4. The goggles of claim 3, wherein the first band is disposed between the first recessed area and the second recessed area, and the second band is disposed between the second recessed area and the third recessed area.

5. The goggles of claim 1, wherein the recessed areas are arranged in adjacent circumferential rows.

6. The goggles of claim 1, wherein the plurality of recessed areas extends along 30-90% of a posterior-anterior length of the gasket.

7. The goggles of claim 1, wherein the gasket includes a thermoplastic rubber.

8. The goggles of claim 1, wherein the plurality of recessed areas are divided into circumferential rows, and a number of circumferential rows including two to six rows.

9. The goggles of claim 1, wherein a crest of a band of the two or more bands is disposed between troughs of recessed areas of the plurality of recessed areas.

10. A gasket for swim goggles, the gasket comprising:

an outer radial surface extending along a periphery of the gasket;

a plurality of recessed areas disposed in the outer radial surface of the gasket, the plurality of recessed areas extending circumferentially along the outer radial surface of the gasket and extending between an anterior edge of the gasket and a posterior edge of the gasket; and two or more bands disposed between the plurality of recessed areas, wherein the plurality of recessed areas and the two or more bands are substantially wave shaped, wherein the two or more bands are separate bands separated by the plurality of recessed areas such that the two or more bands are out of contact with one another.

11. The gasket of claim 10, wherein each of the plurality of recessed areas includes at least one crest and at least one trough, and wherein each band of the two or more bands includes at least one crest and at least one trough.

12. The gasket of claim 11, wherein a first crest of the at least one crests of the two or more bands is disposed between a first trough and a second trough of the at least one troughs of the plurality of recessed areas.

13. The gasket of claim 11, wherein the two or more bands includes a first band and a second band, wherein a trough of the first band is disposed adjacent a crest of the second band.

14. The gasket of claim 10, wherein the substantial wave shape of the two or more bands and the substantial wave shape of the plurality of recessed areas resembles a destructive wave pattern.

15. The gasket of claim 10, wherein a distance between portions of one of the bands and recessed areas of the plurality of recessed areas increases at an outer edge of the gasket.

16. The gasket of claim 10, wherein the plurality of recessed areas and the two or more bands extend along 30-90% of a posterior-anterior length of the gasket.

17. The gasket of claim 10, wherein the gasket includes a thermoplastic rubber.

18. The gasket of claim 10, wherein the two or more bands and the plurality of recessed areas are divided into a plurality of circumferential rows around the outer radial surface, and wherein the plurality of circumferential rows includes two to six rows.

19. Swim goggles including the gasket of claim 10.

20. The gasket of claim 11, wherein the at least one crest of each of the two or more bands includes a rounded concave shape when viewed from the anterior edge of the gasket and the at least one trough of each of the two or more bands includes a rounded convex shape when viewed from the anterior edge of the gasket, and wherein the at least one crest of each of the plurality of recessed areas includes a rounded concave shape when viewed from the anterior edge of the gasket and the at least one trough of each of the plurality of recessed areas includes a rounded convex shape when viewed from the anterior edge of the gasket.

* * * * *